US008376478B2

(12) United States Patent
Weber et al.

(10) Patent No.: US 8,376,478 B2
(45) Date of Patent: Feb. 19, 2013

(54) TAMPER-EVIDENT FASTENER

(75) Inventors: Frank Dean Weber, San Diego, CA (US); Christoph Potakowskyj, Vienna (AT); Johannes Pollhammer, Purkersdorf (AT)

(73) Assignee: CareFusion 303, Inc., San Diego, CA (US)

( * ) Notice: Subject to any disclaimer, the term of this patent is extended or adjusted under 35 U.S.C. 154(b) by 4 days.

(21) Appl. No.: 13/012,762

(22) Filed: Jan. 24, 2011

(65) Prior Publication Data

US 2012/0187815 A1 Jul. 26, 2012

(51) Int. Cl.
*A61B 19/02* (2006.01)
*E05B 65/46* (2006.01)
*B65D 45/16* (2006.01)
*E05C 3/02* (2006.01)
*E05C 3/06* (2006.01)

(52) U.S. Cl. ........ 312/209; 312/215; 220/324; 292/194; 292/198; 292/DIG. 11

(58) Field of Classification Search .................. 312/308, 312/209, 215, 222, 291, 301; 292/194, 219, 292/216, 195, 198, 200, DIG. 11; 220/324
See application file for complete search history.

(56) References Cited

U.S. PATENT DOCUMENTS

2003/0015948 A1* 1/2003 Alexander et al. ............ 312/326
2003/0038053 A1 2/2003 Bramen
2006/0226167 A1* 10/2006 Broadfield et al. ............. 221/98
2008/0142522 A1* 6/2008 Maid ............................ 220/324
2009/0204254 A1* 8/2009 Weber ........................... 700/215
2009/0224638 A1 9/2009 Weber
2011/0285262 A1* 11/2011 Heo et al. ...................... 312/237

FOREIGN PATENT DOCUMENTS

EP 1914094 12/2009
KR 10-2010-0088812 * 8/2010
WO WO 2010087683 A2 * 8/2010

OTHER PUBLICATIONS

International Search Report and Written Opinion for PCT/US2012/022256 mailed Sep. 3, 2012.

* cited by examiner

*Primary Examiner* — David Dunn
*Assistant Examiner* — Ryan A Doyle
(74) *Attorney, Agent, or Firm* — McDermott Will & Emery LLP

(57) ABSTRACT

A container is described. The container includes a receptacle, lid, and fastener. The receptacle includes a latch. The lid is coupled to the receptacle and moves between an open and a closed position. The fastener is coupled to the lid and fastens the lid to the receptacle. The fastener includes first, second, third, and fourth portions. The first portion is coupled to the lid and extends along a first axis that is perpendicular to a plane of the lid when the lid is in the closed position. The second portion is coupled to the first portion and extends along a second axis that is perpendicular to the first axis. The third portion is coupled to the second portion and extends along an axis that is parallel to the first axis. The fourth portion is coupled to the third portion and includes a contact member that couples to the latch.

20 Claims, 7 Drawing Sheets

TAMPER-EVIDENT FASTENER

BACKGROUND

1. Field

The present disclosure generally relates to apparatus and methods for controllably securing a container, and more particularly, to providing physical evidence of unauthorized access to the container.

2. Description of the Related Art

It is well known in the medical community, and in particular, in hospitals, to store medications in a centralized area or station for dispensing and administering the medications to patients. In the past, these stations were often unsecured, allowing access to unauthorized persons. There are several risks associated with unsecured and uncontrolled stations, such as the wrong type or amount of medication being administered to a patient (e.g., such as when medication is taken from an incorrect container in the station), the medication being stolen, or the mixing of medications.

Securable medication dispensing cabinets that seek to address these risks often use individually securable containers in order to lock medication in the containers. These securable containers, however, if accessed inappropriately, often do not indicate any evidence of inappropriate or unauthorized access. For example, when a container lid is subjected to enough force, certain lid fasteners can temporarily deform to an extent that access to the securable container is gained without permanently damaging the fastener. The lack of evidence of damage to the fastener or any other evidence of unauthorized access can be a problem where, for example, incorrect medications are added to or replaced within a container, or medications are stolen from a container in a low traffic area where detection of the unauthorized access will not be identified for extended periods of time.

SUMMARY

The devices disclosed herein, according to certain embodiments, include containers that provide physical evidence of unauthorized access. The containers include fasteners that physically break from the lid of the container due to unauthorized access gained from using physical force to open the lid. In certain embodiments, the containers also include sensors that detect when the fastener has broken, and issue an alert upon the detection.

According to certain embodiments of the present disclosure, a container is disclosed. The container includes a receptacle, a lid, and a fastener. The receptacle includes a latch, and the lid, which is coupled to the receptacle, is configured for movement between an open position allowing access to the receptacle and a closed position restricting access to the receptacle. The fastener is coupled to the lid and configured to fasten the lid to the receptacle when the lid is in the closed position. The fastener includes a first portion, coupled to the lid, which extends along a first axis that is perpendicular to a plane of the lid when the lid is in the closed position. The fastener also includes a second portion, coupled to the first portion, which extends along a second axis that is perpendicular to the first axis. The fastener further includes a third portion, coupled to the second portion, which extends along an axis that is parallel to the first axis. The fastener yet further includes a fourth portion, coupled to the third portion, that includes a contact member configured to couple to the latch.

According to certain embodiments of the present disclosure, a cabinet is disclosed. The cabinet includes a plurality of drawers, each drawer including at least one container. The container includes a receptacle, a lid, and a fastener. The receptacle includes a latch, and the lid, which is coupled to the receptacle, is configured for movement between an open position allowing access to the receptacle and a closed position restricting access to the receptacle. The fastener is coupled to the lid and configured to fasten the lid to the receptacle when the lid is in the closed position. The fastener includes a first portion, coupled to the lid, which extends along a first axis that is perpendicular to a plane of the lid when the lid is in the closed position. The fastener also includes a second portion, coupled to the first portion, which extends along a second axis that is perpendicular to the first axis. The fastener further includes a third portion, coupled to the second portion, which extends along an axis that is parallel to the first axis. The fastener yet further includes a fourth portion, coupled to the third portion, that includes a contact member configured to couple to the latch.

According to certain embodiments of the present disclosure, a method for detecting unauthorized access to a container is disclosed. The method includes providing a plurality of drawers, each drawer including at least one container. The container includes a receptacle, a lid, and a fastener. The receptacle includes a latch, and the lid, which is coupled to the receptacle, is configured for movement between an open position allowing access to the receptacle and a closed position restricting access to the receptacle. The fastener is coupled to the lid and configured to fasten the lid to the receptacle when the lid is in the closed position. The fastener includes a first portion, coupled to the lid, which extends along a first axis that is perpendicular to a plane of the lid when the lid is in the closed position. The fastener also includes a second portion, coupled to the first portion, which extends along a second axis that is perpendicular to the first axis. The fastener further includes a third portion, coupled to the second portion, which extends along an axis that is parallel to the first axis. The fastener yet further includes a fourth portion, coupled to the third portion, that includes a contact member configured to couple to the latch. The method includes breaking at least one of the two intentional break points of the fastener by applying a pull force to the lid parallel to the first axis in a direction distal to the fastener when the contact member is coupled to the latch.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

In the following detailed description, numerous specific details are set forth to provide a full understanding of the present disclosure. It will be obvious, however, to one ordinarily skilled in the art that the embodiments of the present disclosure may be practiced without some of these specific details. In other instances, well-known structures and techniques have not been shown in detail so as not to obscure the disclosure.

Figure 1:
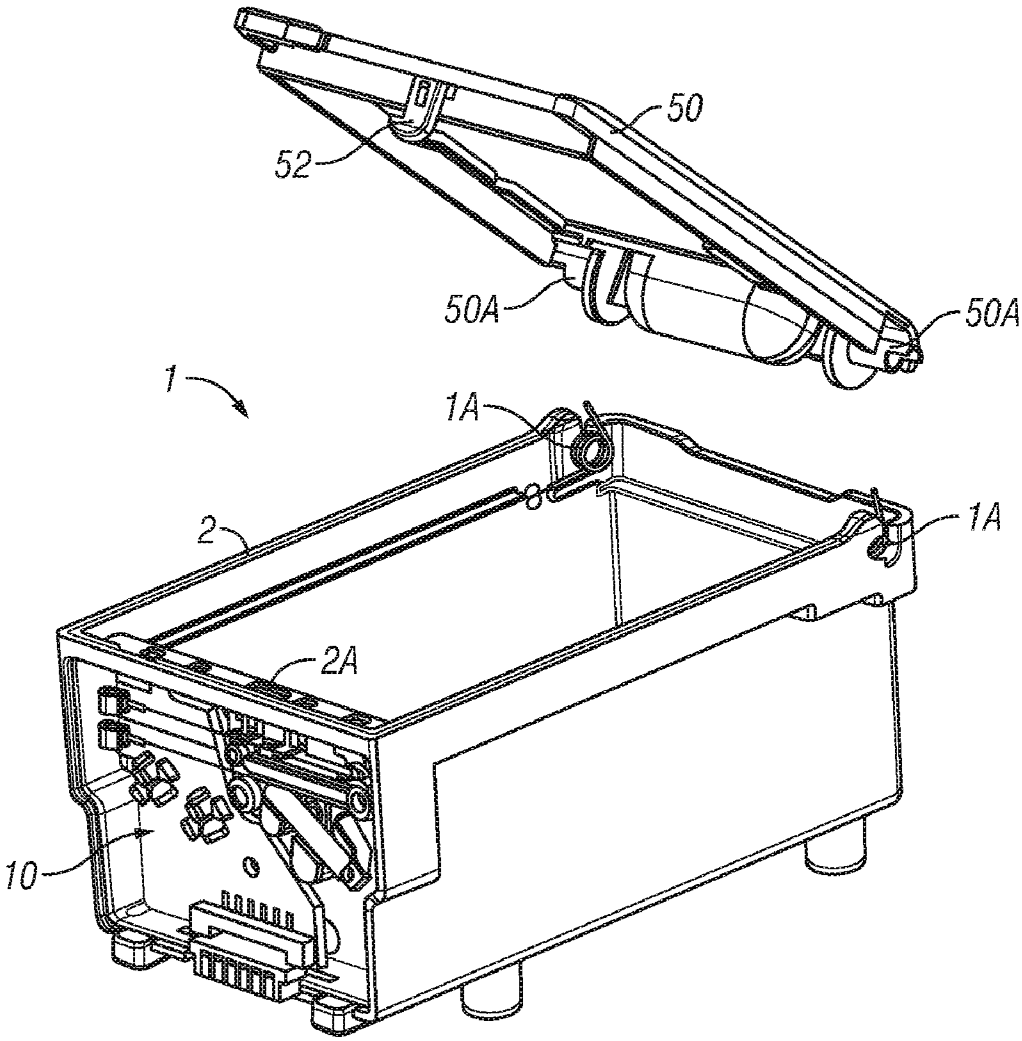
FIG. 1 is a partially exploded view of a lidded container according to certain aspects of this disclosure.

FIG. 1 is a partially exploded view of a lidded container 1 according to certain aspects of this disclosure. The container 1 comprises a body 2 (or "receptacle") and a lid 50 that is coupled to the body 2, although not in this exploded view. In certain embodiments, the lid 50 is hingedly attached to body 2 through engagement of pivot pins 50A with the pin capture features 1A. When the lid 50 is closed, lid fastener 52 (hereinafter "tamper evident fastener" or just "fastener"), which is coupled to the lid 50, passes through the hole 2A in body 2 and comes into proximity with the latch release mechanism 10 that is visible in FIG. 1 within a front compartment of body 2. A front cover plate of body 2 has been omitted to make visible the latch release mechanism 10.

Figure 2:
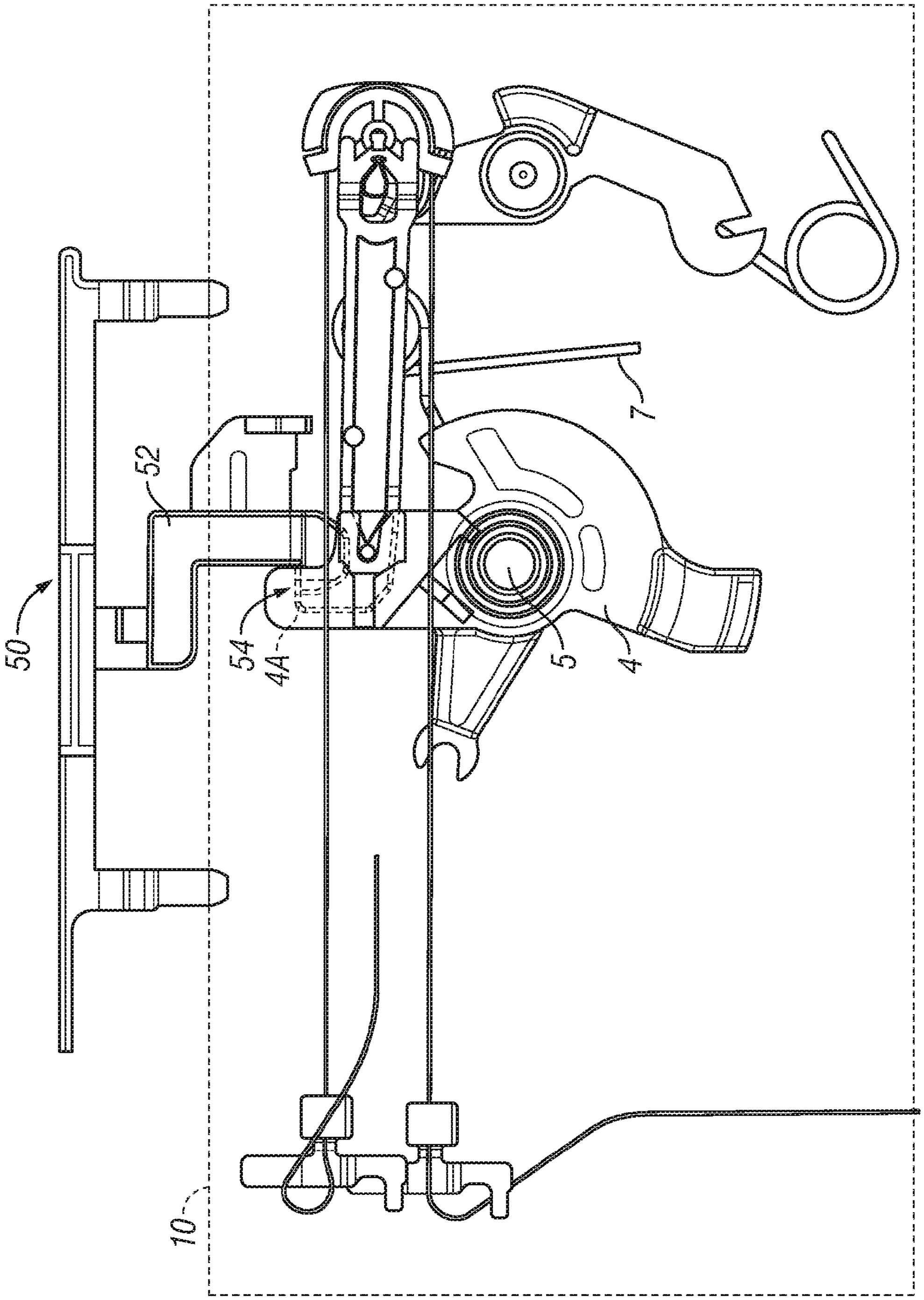
FIG. 2 depicts a tamper evident fastener coupled to a latch of the lidded container of FIG. 1 according to certain aspects of this disclosure.

FIG. 2 depicts the latch release mechanism 10 according to certain aspects of this disclosure. The latch release mechanism 10 is configured to retain lid 50 in a closed position when the lid fastener 52 is coupled to the latch hook 4A in the position shown in FIG. 2. Latch release mechanism 10 is attached to body 2 (not shown in this view) and fixed in position and orientation relative to the lid 50. To reach the illustrated position, latch lever 4 has been rotated in a clockwise direction about a fixed pivot 5 such that latch hook 4A, which is located on the end of one of the arms of latch lever 4, has engaged a contact member 54 of lid fastener 52. Spring 7 applies a force to latch lever 4 that causes a clockwise torque about pivot 5 to be applied to latch lever 4, maintaining the latch lever 4 in the position shown in FIG. 2.

Figure 3:
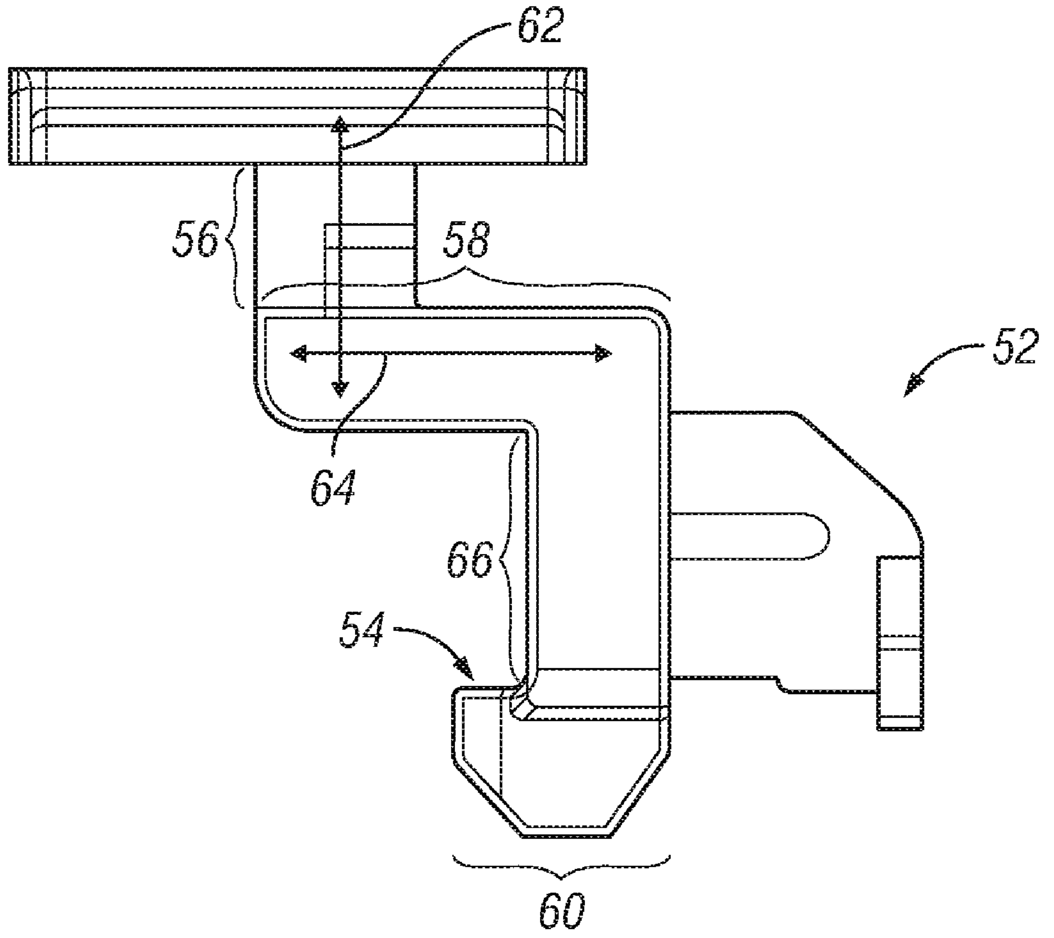
FIG. 3 illustrates an isolated view of the fastener of FIG. 2.

FIG. 3 illustrates an isolated view of the fastener 52. The fastener 52 includes a first portion 56, a second portion 58, a third portion 66, and a fourth portion 60. The first portion 56 is coupled to the lid 50 and extends substantially along a first axis 62 that is perpendicular to the plane of the lid 50. The second portion 58 is coupled to the first portion 56 and extends substantially along a second axis 64 that is perpendicular to the first axis 62. The third portion 66 is coupled to the second portion 64 and extends substantially in parallel to the first axis 62. The fourth portion 60 is coupled to the third portion 66 and includes a contact member 54 configured to couple to the latch hook 4A. In certain embodiments, the contact member 54 is a hook, such as illustrated, for example.

Figure 4A:
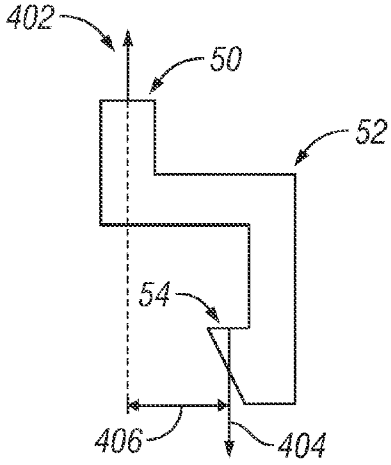
FIG. 4A illustrates the effect of the shape of the fastener of FIG. 2 when unauthorized or forceful access is attempted.
Figure 4B:
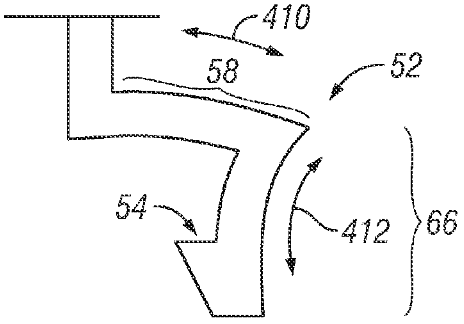
FIG. 4B illustrates how the fastener of FIG. 2 deforms when force is used to gain access to the container.

FIG. 4A illustrates the effect of the shape of the fastener 52 when unauthorized or forceful access is attempted. A first applied force 402 occurs in a direction distal to the contact member 54 because the attempt to force open the lid 50 is in the direction distal to the contact member 54. A second applied force 404 occurs in the direction distal to the lid 50 because the fastener 52 is restrained by the latch hook 4A (not illustrated). The geometry of fastener 52 creates a moment arm 406 between applied forces 402 and 404. The combination of the applied forces 402 and 404 and the moment arm 406 creates a moment in the second portion 58 and third portion 66 of the fastener 52, as shown in FIG. 4E. The moment induces a deflection in the second and third portions 58 and 66 that creates the shape shown (not to scale) in FIG. 4B. The moment arm 406 and/or the stiffness of the first portion 56, the second portion 58, and the third portion 66 can be configured to either provide a net positive rotation of the fourth portion 60 to increase the engagement of the contact member 54 of the fourth portion 60 with the latch hook 4A as the force 402 is increased, or can give a net zero rotation as shown in FIG. 4B. The deflection of fastener 52 attempts to rotate the contact member 54 clockwise with respect to the latch hook 4A (not illustrated), increasing the engagement of the contact member 54 and latch hook 4A. By comparison, a straight vertical fastener would allow the contact member 54 to rotate counterclockwise under the applied forces 402 and 404 and result in the contact member 54 slipping off the latch hook 4A, thereby allowing the lid 50 to open without evidence of tampering.

Figure 4C:
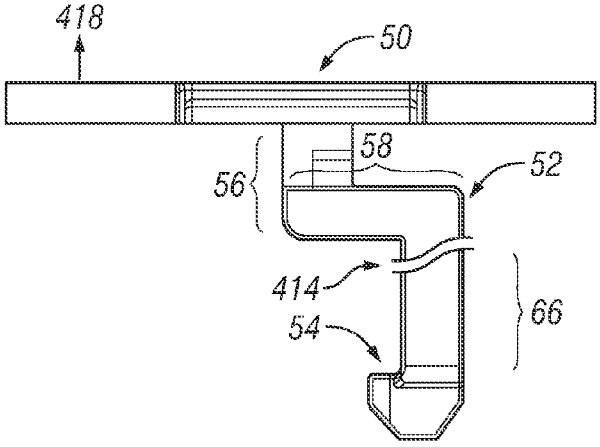
FIGS. 4C and 4D illustrate the fastener of FIG. 2 broken at a first intentional break point and a second intentional break point, respectively.
Figure 4D:
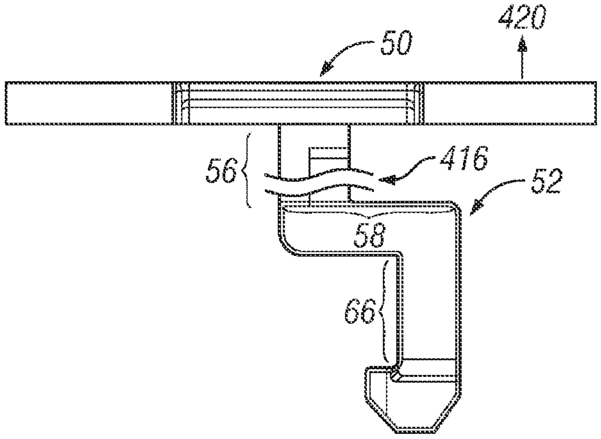
Figure 4E:
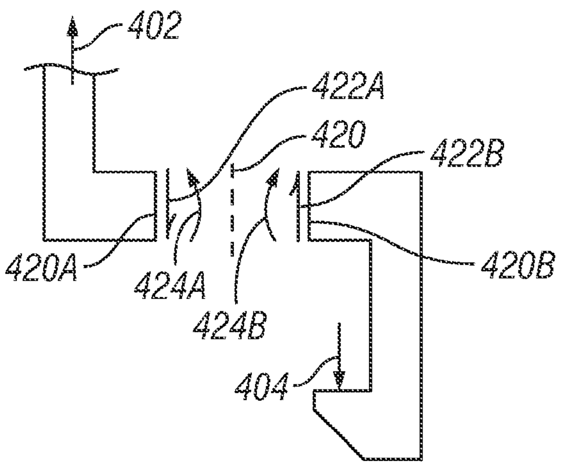
FIG. 4E depicts the forces created within the fastener of FIG. 2 by the deformation shown in FIG. 4B.

FIGS. 4C and 4D illustrate the fastener 52 broken at a first intentional break point 414 or a second intentional break point 416 due to sufficient force being applied to the container 1 to force open the lid 50 and gain access. The fastener 52 is broken because the surface of the contact member 54 did not rotate due to the load force required to break the fastener 52. This occurs because the offset geometry of the fastener 52 decouples the applied moment 406 and applied forces 402 and 404 from the latch hook 4A (not illustrated), and configuration of the geometry to facilitate intentional break points 414 and 416 ensures that the fastener 52 will break before the lid 50 opens. The load at which the intentional break points 414 and 416 fail (i.e., break) is chosen to ensure that the fastener 52 breaks before the fastener 52 deforms enough to release the contact member 54, thereby ensuring that the lid 50 cannot be opened without evidence of the event. The strengths of the first portion 56, the second portion 58, the third portion 66, and the fourth portion 60 are configured such that the load at which the intentional break points 414 and 416 fail (e.g., break) is such to ensure that the fastener 52 breaks before the latch lever 4 breaks or deforms enough to release the contact member 54, thereby ensuring that the lid 50 cannot be opened without evidence of the event.

FIG. 4C illustrates the fastener 52 broken at the first intentional break point 414. The first intentional break point 414 is located at the third portion 66 of the fastener 52 proximal to where the third portion 66 couples to the second portion 58. When the contact member 54 is coupled to the latch 4A (not illustrated), and when a pull force 418 is applied to a portion of the lid 50 parallel to the first axis in a direction distal to the fastener 52 and proximal to the first portion 56 of the fastener 52 and distal to the third portion 66 of the fastener 52 (e.g., by an unauthorized user pulling on the left side of the lid 50), the fastener 52 is configured to break at the first intentional break point 414.

FIG. 4D illustrates the fastener 52 broken at the second intentional break point 416. The second intentional break point 416 is located at the first portion 56 of the fastener 52 proximal to where the first portion 56 couples to the second portion 58. When the contact member 54 is coupled to the latch 4A (not illustrated), and when a pull force 420 is applied to a portion of the lid 50 parallel to the first axis in a direction distal to the fastener 52 and proximal to the first portion 56 of the fastener 52 and distal to the third portion 66 of the fastener 52 (e.g., by an unauthorized user pulling on the right side of the lid 50), the fastener 52 is configured to break at the second intentional break point 416.

FIG. 4E depicts the forces created within the fastener 52 by the deflection shown in FIG. 4B, wherein fastener 52 has been sectioned at plane 420 to reveal the forces and moments at complementary faces 420A and 420B. There is a shear force 422 parallel to the plane 420 resulting in shear forces 422A and 422B applied to faces 420A and 420B respectively. There is also a moment created within second portion 58 that results in moments 424A and 424B applied to faces 420A and 420B respectively.

Figure 4F:
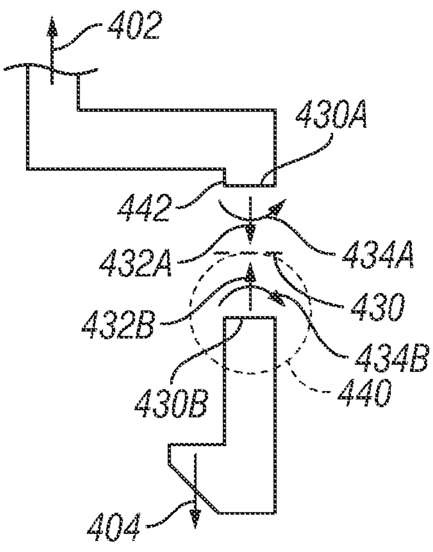
FIG. 4F depicts the forces within the fastener of FIG. 2 at an intentional break point below the corner between the second portion and third portion of the fastener.
Figure 4G:
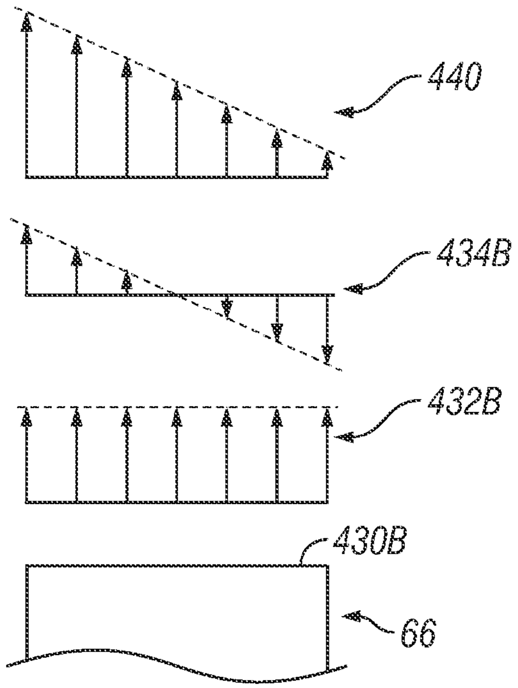
FIG. 4G is an enlarged view of a portion of FIG. 4F.

FIG. 4F depicts the forces within fastener 52 at the intentional break point 442 below the corner between second portion 58 and third portion 66. The fastener 52 has been sectioned at plane 430 to reveal the forces 432A and 432B and moments 434A and 434B at complementary faces 430A and 430B. FIG. 4G is an enlarged view of face 430B, wherein the force 432B is shown as an even distribution of tension forces across the face 430B, wherein the net vertical force of moment 434B is zero. The sum of the distributed forces of force 432B and moment 434B creates the force distribution 440. It can be seen that a maximum tension force is created at point 442 on the inside edge of face 430B. The design of fastener 52 is such that this force will exceed the material strength of the fastener 42 and breaks the fastener 52 before the fastener 52 deforms further and disengages from latch hook 4A.

Hence, with the above embodiments, prior to opening the lid 50 forcibly, the fastener 52 will be damaged at one of the intentional break points 414 and 416. As described below, in certain embodiments, such breaks can be detected with a sensor 502.

Figure 5:
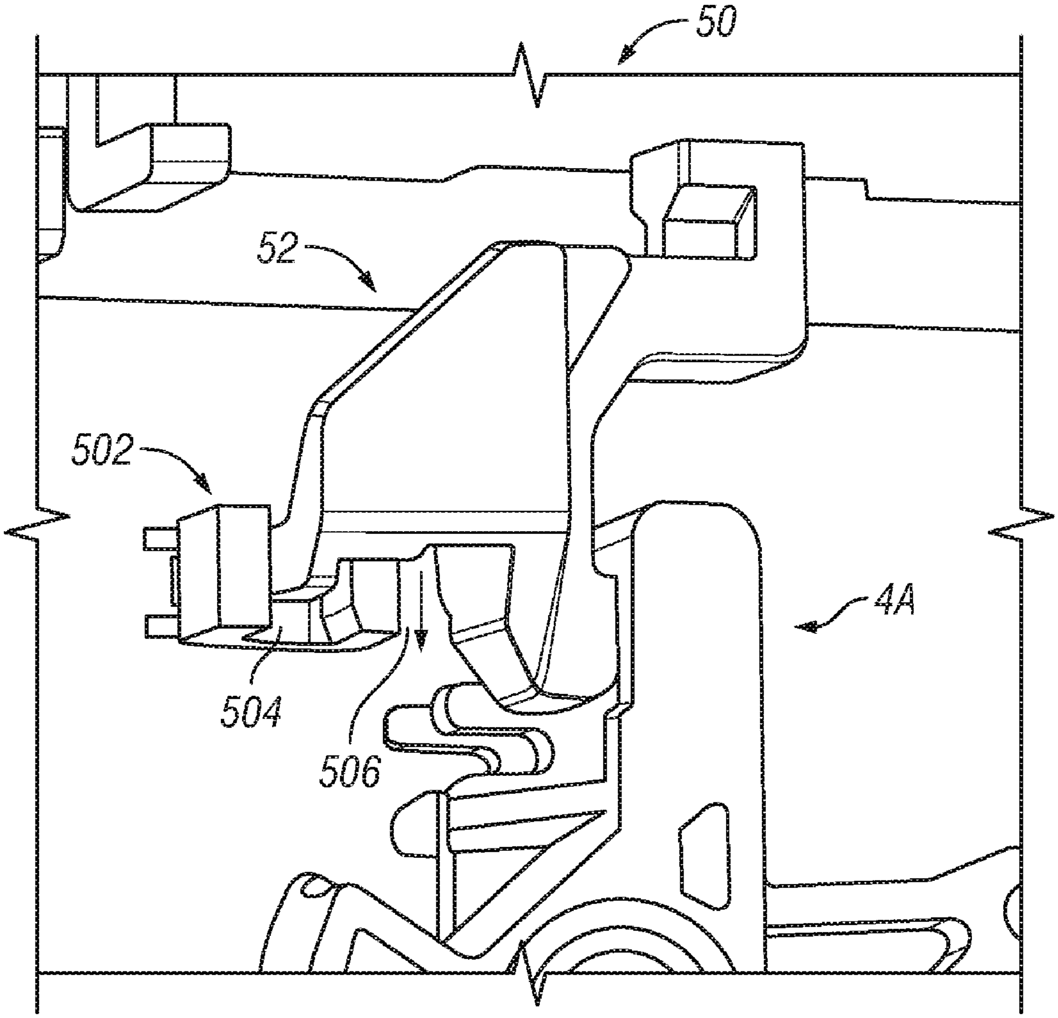
FIG. 5 illustrates a sensor configured to detect when the fastener has broken from the lid of the lidded container of FIG. 1.

FIG. 5 illustrates a sensor 502 configured to detect when the fastener 52 has been broken. In certain embodiments, the sensor 502 is a photointerrupter, although other types of sensors can be used. In certain embodiments, fastener 52 includes a flag 504. If the fastener 52 breaks from the lid 50 (e.g., at one of the intentional break points 414 and 416), the fastener 52 and flag 504 fall in the direction 506 away from the lid 50 and towards the latch hook 4A. The optical path of the sensor 502 is opened by the falling flag 504, putting the sensor 502 into a "lid-open state." In certain embodiments, the lid-open state triggers an audible, visible, and/or electronic communication alert to indicate that the lidded container 1 is no longer secure due to unauthorized access. The signal can be sent to a controller/remote server 500 of an ADM 100 (see FIG. 6), and also or alternatively, to a central server or security station to alert other personnel of the forcible and potentially unauthorized access.

Figure 6:
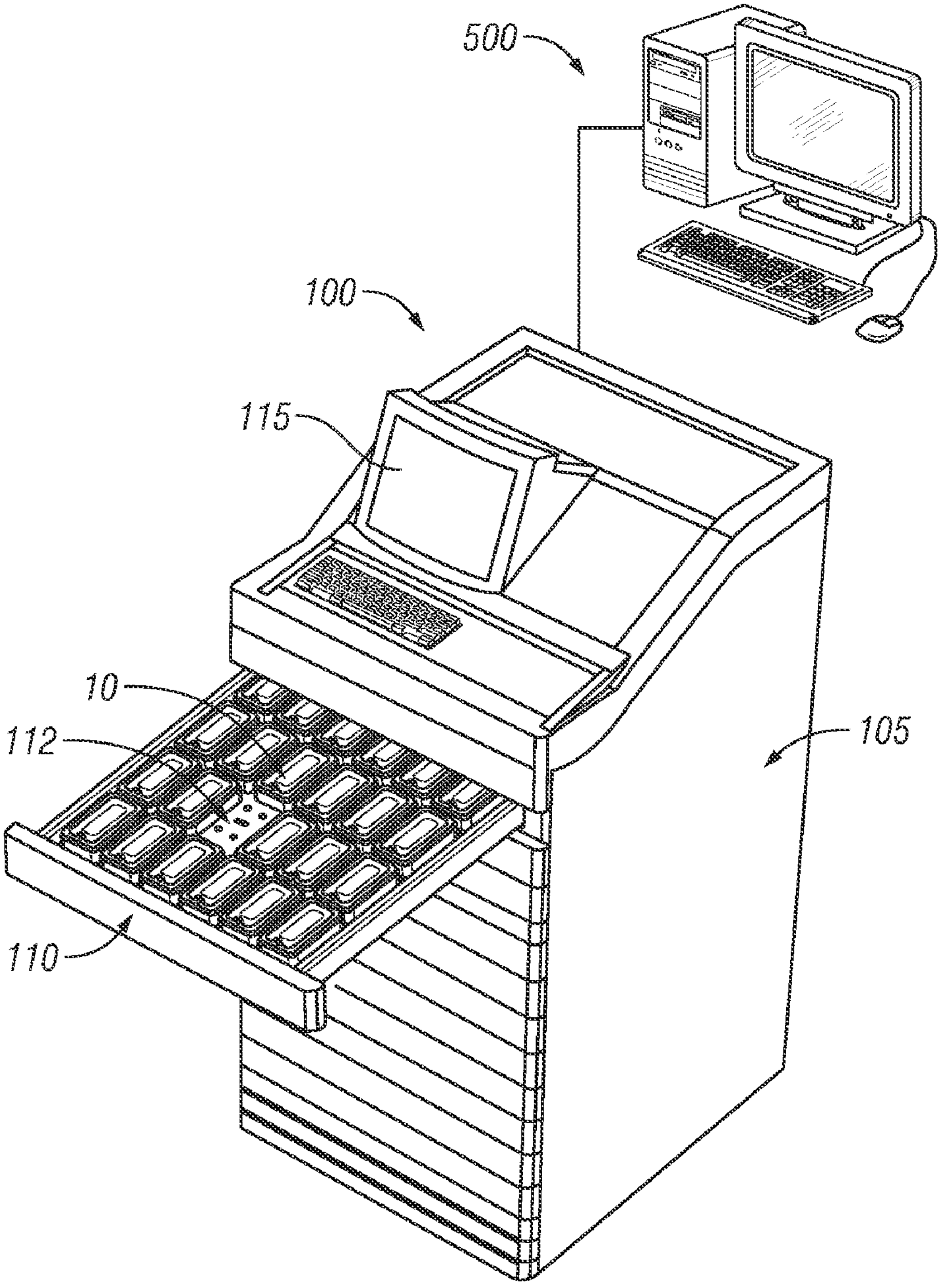
FIG. 6 illustrates an exemplary automated dispensing machine (ADM) that includes removable lidded containers that include the fastener of FIG. 2.

FIG. 6 illustrates an exemplary ADM 100 that includes removable lidded containers 1 that include fasteners 52 according to certain aspects of this disclosure. The ADM 100 includes a cabinet 105 with a controller 115 that is, in this example, housed in the top structure of the ADM 100. The controller 115 includes a processor with a memory (not shown), a display, a keyboard and touch screen input devices, a power supply (not shown), and communication modules (not shown) that couple the processor to the internal components of the ADM 100 and to external networks. In certain embodiments, the ADM 100 includes a barcode scanner (not shown) that is fixedly or removably mounted to the top structure or cabinet. The ADM 100 also includes a drawer 110 that is configured to accept the lidded containers 1 from FIG. 1, wherein the lidded containers 1 and the drawer 110 both include complementary mating connectors that couple the lidded containers 1 to the controller 115 when the lidded containers 1 are accepted by the drawer 110. The drawer 110 has multiple locations 112 configured to accept a lidded container 1. In certain embodiments, the lidded containers 1 are attached to fixed parts of the cabinet 105, such as a shelf or inclined surface. In certain embodiments, the lidded containers 1 are not separate from the structure of the cabinet 105, wherein the equivalent to the body 2 of FIG. 1 is integrally formed into the structure of the cabinet 105. In certain embodiments, the equivalent to the body 2 of FIG. 1 is integrally formed into the structure of the drawer 110, wherein the compartments formed by the bodies 2 in such a structure have individual lids 50 mounted to the common drawer structure. In certain embodiments, the cabinet 105 is a smaller structure having only a few drawers 110, wherein the storage capacity of the ADM 100 is suitable for a single patient rather than a plurality of patients. In certain embodiments, the cabinet 105 is mounted to and supported by a wall. In certain embodiments, the ADM 100 is communicatively connected to a controller/remote server 500.

In summary, the disclosed fastener 52 provides physical evidence of unauthorized access because the fastener 52 is configured to break at intentional break points 414 and 416 if sufficient force is used to open the lid 50 to gain access to the lidded container 1. The fastener 52 is configured to break at the predetermined intentional break points 414 and 416 due to the unique geometry of the fastener 52, which is configured to deform in a shape that requires the fastener 52 to break in order for unauthorized access to the lidded container 1 to be achieved.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A container comprising:

a receptacle comprising a latch;

a lid coupled to the receptacle, and configured for movement between an open position allowing access to the receptacle and a closed position restricting access to the receptacle;

a fastener configured to releasably secure the lid in the closed position and to break at one or more of a first intentional break point and a second intentional break point in response to application of a first force on the fastener, the fastener comprising:

a first portion comprising a first end that is fixedly attached to the lid and a second end, the first portion extending from the lid along a first axis that is perpendicular to a plane of the lid when the lid is in the closed position;

a second portion comprising a first end that is fixedly attached to the second end of the first portion and a second end, the second portion extending from the first portion along a second axis that is perpendicular to the first axis;

a third portion comprising a first end that is fixedly attached to the second end of the second portion and a second end, the third portion extending from the second portion along an axis that is parallel to the first axis; and a fourth portion comprising a first end that is fixedly attached to the second end of the third portion, the fourth portion extending from the second end of the third portion along an axis that is parallel to the second axis, the fourth portion comprising a contact member configured to couple to the latch;

wherein the third portion further comprises the first intentional break point and the first portion comprises the second intentional break point, and wherein the first force is applied to the contact member in a direction parallel to the first axis, and wherein when a pull force is applied to a portion of the lid proximal to the first portion of the fastener and distal to the third portion of the fastener, the fastener is configured to break at the second break point.

2. The container of claim 1, wherein when the pull force is applied to a portion of the lid distal to the first portion of the fastener and proximal to the third portion of the fastener, the fastener is configured to break at the first break point.

3. The container of claim 1, further comprising a sensor configured to detect when the fastener has broken.

4. The container of claim 1, wherein the contact member comprises a hook.

5. A container comprising:

a receptacle comprising a latch;

a lid coupled to the receptacle, and configured for movement between an open position allowing access to the receptacle and a closed position restricting access to the receptacle;

a fastener configured to releasably secure the lid in the closed position and to break at one or more of a first intentional break point and a second intentional break point in response to application of a first force on the fastener, the fastener comprising:

a first portion comprising a first end that is fixedly attached to the lid and a second end, the first portion extending from the lid along a first axis that is perpendicular to a plane of the lid when the lid is in the closed position;

a second portion comprising a first end that is fixedly attached to the second end of the first portion and a second end, the second portion extending from the first portion along a second axis that is perpendicular to the first axis;

a third portion comprising a first end that is fixedly attached to the second end of the second portion and a second end, the third portion extending from the second portion along an axis that is parallel to the first axis; and a fourth portion comprising a first end that is fixedly attached to the second end of the third portion, the fourth portion extending from the second end of the third portion along an axis that is parallel to the second axis, the fourth portion comprising a contact member configured to couple to the latch;

wherein the third portion further comprises the first intentional break point and the first portion comprises the second intentional break point, and wherein the first force is applied to the contact member in a direction parallel to the first axis, and wherein when a pull force is applied to a portion of the lid distal to the first portion of the fastener and proximal to the third portion of the fastener, the fastener is configured to break at the first break point.

6. The container of claim 5, wherein when the pull force is applied to a portion of the lid proximal to the first portion of the fastener and distal to the third portion of the fastener, the fastener is configured to break at the second break point.

7. The container of claim 5, further comprising a sensor configured to detect when the fastener has broken.

8. The container of claim 5, wherein the contact member comprises a hook.

9. A cabinet comprising:

a plurality of drawers, each drawer comprising:

at least one container, comprising:

a receptacle comprising a latch;

a lid coupled to the receptacle, and configured for movement between an open position allowing access to the receptacle and a closed position restricting access to the receptacle;

a fastener configured to releasably secure the lid in the closed position and to break at one or more of a first intentional break point and a second intentional break point in response to application of a first force on the fastener, the fastener comprising:

a first portion comprising a first end that is fixedly attached to the lid and a second end, the first portion extending from the lid along a first axis that is perpendicular to a plane of the lid when the lid is in the closed position;

a second portion comprising a first end that is fixedly attached to the second end of the first portion and a second end, the second portion extending from the first portion along a second axis that is perpendicular to the first axis;

a third portion comprising a first end that is fixedly attached to the second end of the second portion and a second end, the third portion extending from the second portion along an axis that is parallel to the first axis; and a fourth portion comprising a first end that is fixedly attached to the second end of the third portion, the fourth portion extending from the second end of the third portion along an axis that is parallel to the second axis, the fourth portion comprising a contact member configured to couple to the latch;

wherein the third portion further comprises the first intentional break point and the first portion comprises the second intentional break point, and wherein the first force is applied to the contact member in a direction parallel to the first axis, and wherein when a pull force is applied to a portion of the lid proximal to the first portion of the fastener and distal to the third portion of the fastener, the fastener is configured to break at the second break point.

10. The cabinet of claim 9, wherein when the pull force is applied to a portion of the lid distal to the first portion of the fastener and proximal to the third portion of the fastener, the fastener is configured to break at the first break point.

11. The cabinet of claim 9, further comprising a sensor configured to detect when the fastener has broken.

12. The cabinet of claim 9, wherein the contact member comprises a hook.

13. A cabinet comprising:

a plurality of drawers, each drawer comprising:

at least one container, comprising:

a receptacle comprising a latch;

a lid coupled to the receptacle, and configured for movement between an open position allowing access to the receptacle and a closed position restricting access to the receptacle;

a fastener configured to releasably secure the lid in the closed position and to break at one or more of a first intentional break point and a second intentional break point in response to application of a first force on the fastener, the fastener comprising:

a first portion comprising a first end that is fixedly attached to the lid and a second end, the first portion extending from the lid along a first axis that is perpendicular to a plane of the lid when the lid is in the closed position;

a second portion comprising a first end that is fixedly attached to the second end of the first portion and a second end, the second portion extending from the first portion along a second axis that is perpendicular to the first axis;

a third portion comprising a first end that is fixedly attached to the second end of the second portion and a second end, the third portion extending from the second portion along an axis that is parallel to the first axis; and a fourth portion comprising a first end that is fixedly attached to the second end of the third portion, the fourth portion extending from the second end of the third portion along an axis that is parallel to the second axis, the fourth portion comprising a contact member configured to couple to the latch;

wherein the third portion further comprises the first intentional break point and the first portion comprises the second intentional break point, and wherein the first force is applied to the contact member in a direction parallel to the first axis, and wherein when a pull force is applied to a portion of the lid distal to the first portion of the fastener and proximal to the third portion of the fastener, the fastener is configured to break at the first break point.

14. The cabinet of claim 13, wherein when the pull force is applied to a portion of the lid proximal to the first portion of the fastener and distal to the third portion of the fastener, the fastener is configured to break at the second break point.

15. The cabinet of claim 13, further comprising a sensor configured to detect when the fastener has broken.

16. The cabinet of claim 13, wherein the contact member comprises a hook.

17. A method for detecting unauthorized access to a container, the method comprising the steps of:

providing a plurality of drawers, each drawer comprising:

at least one container, comprising:

a receptacle comprising a latch;

a lid coupled to the receptacle, and configured for movement between an open position allowing access to the receptacle and a closed position restricting access to the receptacle; and a fastener configured to releasably secure the lid in the closed position and to break at one or more of a first intentional break point and a second intentional break point in response to application of a first force on the fastener, the fastener comprising:

a first portion comprising a first end that is fixedly attached to the lid and a second end, the first portion extending from the lid along a first axis that is perpendicular to a plane of the lid when the lid is in the closed position, wherein the second intentional break point is located within the first portion of the fastener;

a second portion comprising a first end that is fixedly attached to the second end of the first portion and a second end, the second portion extending from the first portion along a second axis that is perpendicular to the first axis;

a third portion comprising a first end that is fixedly attached to the second end of the second portion and a second end, the third portion extending from the second portion along an axis that is parallel to the first axis, wherein the first intentional break point is located within the third portion of the fastener; and a fourth portion comprising a first end that is fixedly attached to the second end of the third portion, the fourth portion extending from the second end of the third portion along an axis that is parallel to the second axis, the fourth portion comprising a contact member configured to couple to the latch;

wherein when a pull force is applied to a portion of the lid proximal to the first portion of the fastener and distal to the third portion of the fastener, the fastener is configured to break at the second break point, and breaking at least one of the first and second intentional break points of the fastener by applying the pull force to the lid parallel to the first axis in a direction distal to the fastener when the contact member is coupled to the latch.

18. The cabinet of claim 17, wherein when the pull force is applied to a portion of the lid distal to the first portion of the fastener and proximal to the third portion of the fastener, the fastener is configured to break at the first break point.

19. A method for detecting unauthorized access to a container, the method comprising the steps of:

providing a plurality of drawers, each drawer comprising:

at least one container, comprising:

a receptacle comprising a latch;

a lid coupled to the receptacle, and configured for movement between an open position allowing access to the receptacle and a closed position restricting access to the receptacle; and a fastener configured to releasably secure the lid in the closed position and to break at one or more of a first intentional break point and a second intentional break point in response to application of a first force on the fastener, the fastener comprising:

a first portion comprising a first end that is fixedly attached to the lid and a second end, the first portion extending from the lid along a first axis that is perpendicular to a plane of the lid when the lid is in the closed position, wherein the second intentional break point is located within the first portion of the fastener;

a second portion comprising a first end that is fixedly attached to the second end of the first portion and a second end, the second portion extending from the first portion along a second axis that is perpendicular to the first axis;

a third portion comprising a first end that is fixedly attached to the second end of the second portion and a second end, the third portion extending from the second portion along an axis that is parallel to the first axis, wherein the first intentional break point is located within the third portion of the fastener; and a fourth portion comprising a first end that is fixedly attached to the second end of the third portion, the fourth portion extending from the second end of the third portion along an axis that is parallel to the second axis, the fourth portion comprising a contact member configured to couple to the latch;

wherein when a pull force is applied to a portion of the lid distal to the first portion of the fastener and proximal to the third portion of the fastener, the fastener is configured to break at the first break point, and breaking at least one of the first and second intentional break points of the fastener by applying the pull force to the lid parallel to the first axis in a direction distal to the fastener when the contact member is coupled to the latch.

20. The cabinet of claim 19, wherein when the pull force is applied to a portion of the lid proximal to the first portion of the fastener and distal to the third portion of the fastener, the fastener is configured to break at the second break point.

* * * * *